United States Patent [19]

Politi et al.

[11] Patent Number: 5,210,215

[45] Date of Patent: May 11, 1993

[54] TRYPTOPHANE AND 3-INDOLEPYRUVIC ACID, METHODS OF PRODUCTION THEREFOR

[75] Inventors: Vincenzo Politi; Giovanna De Luca; Giovanni Di Stazio; Mario Materazzi, all of Rome, Italy

[73] Assignee: Polifarma S.p.A., Rome, Italy

[21] Appl. No.: 584,128

[22] Filed: Sep. 18, 1990

[30] Foreign Application Priority Data

Oct. 4, 1989 [IT] Italy .............................. 48426 A/89

[51] Int. Cl.$^5$ .................. C07D 209/18; C07D 209/20
[52] U.S. Cl. .................................. 548/494; 548/496; 548/497; 548/502
[58] Field of Search ................ 548/494, 502, 496, 497

[56] References Cited

U.S. PATENT DOCUMENTS 4,551,471  11/1985  De Luca et al. ..................... 548/494
4,808,728  11/1985  De Luca et al. ..................... 548/494

OTHER PUBLICATIONS

Lancet, II, 140–143, (1985).
Neuroscience Letters, vol. 48, (1984), pp. 273–278.

Primary Examiner—David B. Springer
Attorney, Agent, or Firm—Birch, Stewart, Kolasch & Birch

[57] ABSTRACT

3-indolepyruvic acid derivatives substituted on the benzene moiety show good antagonizing activity on excitatory aminoacids and on free radicals, for which reason they are therapeutic agents in cerebral and peripheral degenerative pathologies. Their method of production by passage through the corresponding substituted triptophane.

7 Claims, No Drawings

TRYPTOPHANE AND 3-INDOLEPYRUVIC ACID, METHODS OF PRODUCTION THEREFOR

BACKGROUND OF THE INVENTION

1. Field of Invention

The present invention refers to 3-indolepyruvic acid derivatives, substituted on the benzene moiety, along with a method for their production and their therapeutic use.

The compounds according to the present invention are characterized by the presence of substituents on the benzene ring of the indole nucleus and are represented by the general formula I

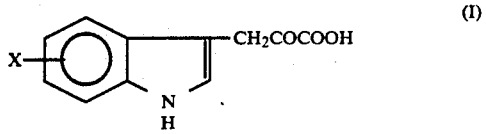

in which X is methyl, methoxy, hydroxyl or halogen.

2. Description of the Prior Art 3-indolepyruvic acid has shown itself to possess extraordinary biological and pharmacological activity because, having double bonds conjugated into enole configuration, it is capable of capturing oxygen free radicals (especially OH) and therefore of transforming itself into kynurenic acid, which in international literature appears as the most important physiological antagonist of excitatory amino acids. Said amino acids are substances capable of irreversibly destroying neurons in degenerative diseases, such as cerebral ischemia, aging, epilepsy, etc. (see for example Lancet, II, 140-143, 1985; Neurosience Letters 48, 273-278, 1984).

The properties of 3-indolepyruvic acid as a capturer of free radicals have been described in the published European application No. 0362152.

The capability of 3-indolepyruvic acid to transform itself into kynurenic acid has, on the other hand, been described in the international patent application WO88/09789. In the latter application have also been described several derivatives of 3-indolepyruvic acid, obtained by esterification or amidation of the carboxylic acid.

SUMMARY OF THE INVENTION

It has now been found, which forms the object of the present invention, that 3-indolepyruvic acid derivatives obtained by substitutions on the benzene ring of the indole nucleus, are compounds of even greater interest, as they can antagonize the harmful effects of oxygen free radicals and of excitatory amino acids in a manner even more efficacious than 3-indolepyruvic acid and its derivatives described in the prior art.

The of the present invention are therefore the said derivatives represented by formula (I), along with their method of production, which consists in starting from benzene, firstly performing the substitutions on the ring, then transfroming the substituted benzene into a substituted indole, then transforming the latter into a substituted tryptophane, and finally operating on the latter to obtain 3-indolepyruvic acid derivatives.

A further object of the present invention is the pharmacological use of said derivatives as antagonists for excitatory amino acids and free radicals and thus their use in cerebral and peripheral degenerative pathologies.

SYNTHESIS OF THE COMPOUNDS OF FORMULA (I)

The direct insertion of a substituent into the benzene moiety of indolepyruvic acids is known to be prohibited by the characteristics of intrinsic instability of the molecule (see for example Chemical Review 83, 321, 1987). For similar reasons the direct substitution on the tryptophan molecule is also impossible.

For the preparation of benzenoid substituted indolepyruvic acids, according to the present invention, the method starts with a substituted benzene, transforming it into a substituted indole, then passing it to the corresponding substituted tryptophan and finally preparing the substituted indolepyruvic acids.

The synthesis of the indole ring is well documented by a rich chemical literature (see for example "Synthesis of the indole nucleus" in : Indoles, part I, J, Wiley & Sons, 1972; "The Chemistry of indoles", Chapter III, Academic Press, 1970; "Contemporary heterocyclic chemistry", Chapter V, J. Wiley and Sons, 1982; etc.).

In general, all the synthetic approaches that want positions 2 and 3 of the indole ring free or easily freed, start from suitably substituted benzene and differ from one another only in the sequence of reactions which bring about the formation of the hetero-aromatic (pyrrolic) part of the indole ring.

The transformation of the indole ring to tryptophan is also supported by a large amount of literature. Said transformation can be brought down to two general methods, which are resumed in the following table:

First method of synthesis:

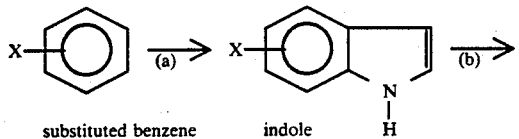

substituted benzene        indole

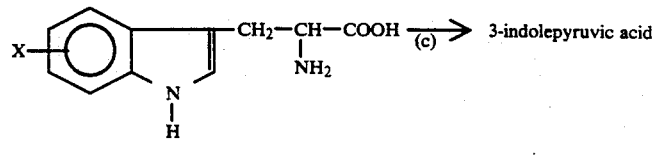

tryptophan

Second method of synthesis:

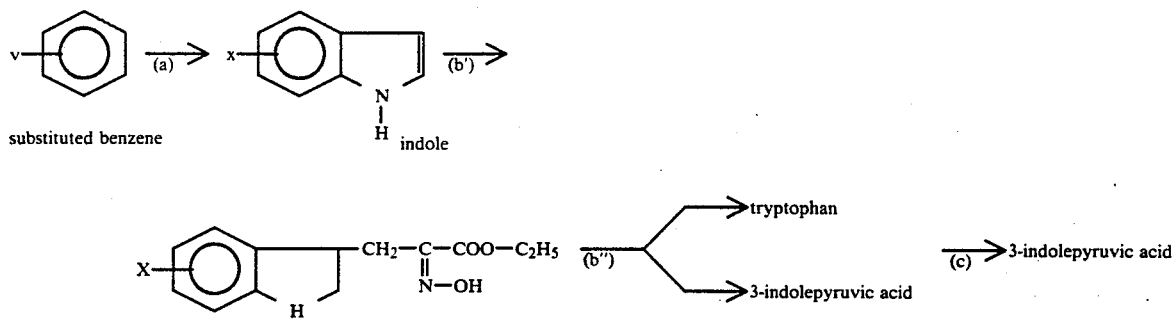

The first method of synthesis shows the intermediate transformation of the indole into the corresponding Mannich base, that is gramine, thus taking advantage of the capacity of the Mannich base to condense, in an alkaline environment, with derivatives of a malonic type (alkylation of compounds with active methylene).

See for example "The Chemistry of the amino acids" chapter 39, J. Wiley and Sons, 1961; "Chemistry and biochemistry of the amino acids" chapter 7, Chapman & Hall, 1985.

The second method of synthesis on the contrary shows the direct alkylization of the indole ring, preformed with a suitable structure containing the amino acid part of tryptophan in a masked form (see for example J. Organic Chemistry 49, 540, 2657 and 4409, 1984; Tetrahedron 38, 2051, 1982). Said second method furthermore permits the direct transformation of the intermediate oxylimine-indole into the corresponding indolepyruvic acid derivate, along with the passage through the corresponding tryptophan.

For the transformation of the substituted tryptophan on the benzene ring into the corresponding 3-indolepyruvic acid derivative various methods can be used. A particularly advantageous method is described.

It has been found that tryptophan, both in the form of the individual L- and D-isomers, and the D,L-mixture, can be used as a starting compound for a chemical synthesis of 3-indolepyruvic acid with high yields.

A process for the production of indolepyruvic acid or the 5-hydroxy derivative thereof (is) characterized by the steps of:

reacting tryptophan or 5-hydroxy tryptophan, respectively, or a lower alkyl ester thereof, with a pyridine aldehyde in an essentially anhydrous polar organic solvent in the presence of a tertiary amine base; and hydrolyzing the resulting reaction mixture with a strongly acidic aqueous solution to obtain a precipitate consisting essentially of indolepyruvic acid or its 5-hydroxy derivative, respectively.

Consequently the invention is characterized by the use of an agent having a high dehydrating power with respect to a coupling reaction, which reaction is assumed to lead to a schiff base.

As aldehydes to be reacted with the alpha-aminoacid, aromatic aldehydes are preferred.

Representatives of said aldehydes are isonicotinaldehyde and hydroxy derivatives of benzaldehyde, which are particularly preferred.

The solvent used in the reaction can be an anhydrous solvent. Representatives thereof are dimethylformamide (DMF) and acetonitrile. A hydrous solvent can also be used. Representatives of this are DMF and methanol.

The reaction can be carried out at room temperature with good results, depending anyway on the particular species of amino acids to be reacted.

The process has shown itself particularly effective for the production of 3-indolepyruvic acid, in that the reaction runs with very high yields (higher than 50%) with respect to the tryptophan or its ester. However, as stated above, the process is of more general validity, as tryptophan which is substituted in 5-position has also shown to react under the same conditions.

EXAMPLES OF PREPARATION

Preparation of Indole Derivatives

Where possible, the substituted indole derivatives on the benzene ring have been acquired from commercial sources. For example the 4- and 6-chloroindole, 5-bromoindole, 4-, 5- and 7-methylindole, 4- and 5-hydroxylindole, 5- and 6-fluoroindole have been obtained from Sigma Chemical. 5-chloroindole from Janssen Chimica; 6-methylindole from Aldrich, etc.

Otherwise they can be obtained by the classical methods previously cited, starting from the corresponding substituted benzene.

In this way general compounds have been obtained having formula II

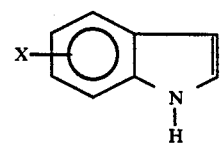

II in which X has the meaning indicated above.

Preparation of Gramine Derivatives

The substituted indole derivatives of formula (II) were made to react with dimethylamine and aqueous formaldehyde to form general compounds of formula III

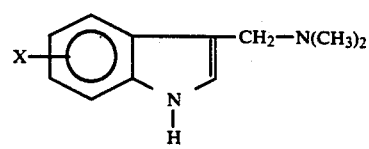

III in which X has the meaning indicated above.

EXAMPLE 1

Synthesis of the compound 6-chloro-3(dimethylaminomethyl)-indole, or 6-chloro-gramine Glacial acetic acid (0,4 ml) was added dropwise to an aqueous solution at 33% (w/v) of dimethylamine (0,4 ml), cooled in an ice bath, at a speed so as not to exceed a temperature of 5° C. Under continuous stirring and in an ice bath, were added in succession an aqueous solution of formaldehyde (0,2 ml at 40% w/v) and then 420 mg of 6-chloroindole, which in approximately 10 minutes dissolved in the reaction mixture with the development of heat. The reaction mixture was left at room temperature for approximately 16 hours. The solution was then poured into NaOH 2N (10 ml) and extracted with ethyl ether (3×15 ml). The organic phase was washed with saturated NaCl/H$_2$O (2×10 ml) and dried on anhydrous magnesium sulphate overnight. On evaporation of the solvent, a residue was obtained, of practically pure 6-chloro-gramine, equal to 550 mg (yield 95%).

EXAMPLE 2

Preparation of 6-chloro-tryptophan

Under inert atmosphere and rapid stirring 52 mg of NaOH are pulverized into anhydrous xylene (20 ml), heating the suspension at approximately 90° C. 550 mg of 6-chlorogramine (prepared as described in example 1) and 460 mg of ethyl-acetamido-acetate are then added. The mixture is refluxed for approximately 7 hours and the development of dimethylamine, extremely vigorous at the start of the heating, practically ceases after about 6 hours of heating. The reaction mixture is cooled for 12 hours at 5° C. and then filtered to recover the abundant precipitate. This crude solid is treated with a hot solution of benzene/absolute ethanol, and the insoluble material is hot-filtered. The solution is left to rest at 5° C. for 12 hours. Crystals slowly separate, which are filtered and dried. 750 mg of ethyl-α-acetamido-α-cyano-β-(6-chloro-indole-3-yl)-propioanate are recovered, with a yield of 84%. 600 mg of this compound are added to 15 ml of water, containing 40 mg of NaOH and the mixture is boiled for 24 hours. During this time the solid material dissolves and ammonia is developed. After the reflux time, the reaction mixture is cooled at room temperature and neutralized with acetic acid at 50%. It is filtered, recovering and washing with cold water the solid which has formed. After drying 410 mg of 6-chloro-DL-tryptophan are recovered, with a yield of 95%.

EXAMPLE 3

In a similar way tryptophan of general formula IV were prepared

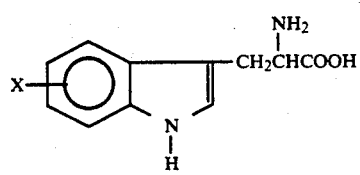

IV in which X has the meaning indicated above.

EXAMPLE 4

Preparation of 6-chloro-indole-3-yl-pyruvic acid

To 600 mg of 6-chloro-DL-tryptophan, suspended in 5 ml of methanol, are added, at room temperature, 0,230 ml of triethylamine and the mixture is stirred for approximately 10 minutes. Then, rapidly and under stirring, pyridine-4-carboxyaldehyde (0,240 ml) is added. After approximately 5 minutes, total dissolution of the suspension is obtained. Stirring is continued for 10 minutes. 122 mg of anhydrous ZnCl2 are then added, stirred for 10 minutes, followed by 0,490 ml of 1,8-diazabicyclo-(5,4,0)-undec-7-ene. The solution becomes orange-red in colour. It is left under stirring for approximately 80-90 minutes at room temperature. The limpid red solution is then quickly added dropwise and under rapid stirring to 100 ml of HCl 1N preheated to 50° C. After approximately 10 minutes from completion of the addition a spontaneous precipitation occurs, increasing in time, of a yellowish solid. The mixture is left for a further 20 minutes at 55° C., then for approximately 3 hours it is cooled to room temperature. The abundant precipitate is filtered, washed with acidic water and dried. 195 mg are recovered, with a yield of 54%.

EXAMPLE 5

In a similar manner are prepared compounds of the general formula I, among which are indicated as examples:
4-chloro-indole-3-yl-pyruvic,
6-chloro-indole-3-yl-pyruvic,
5-bromo-indole-3-yl-pyruvic,
4-methyl-indole-3-yl-pyruvic,
5-methyl-indole-3-yl-pyruvic,
7-methyl-indole-3-yl-pyruvic,
4-hydroxy-indole-3-yl-pyruvic,
5-hydroxy-indole-3-yl-pyruvic,
5-fluoro-indole-3-yl-pyruvic,
6-fluoro-indole-3-yl-pyruvic,
5-chloro-indole-3-yl-pyruvic,
6-methyl-indole-3-yl-pyruvic.

Synthesis Through Indole Hydroxylimine Intermediates (Second Method of Synthesis)

Derivatives of general formula I can also be obtained by means of the second method of synthesis mentioned herein above. This comprises an first condensation reaction, in a environment basic for anhydrous Na$_2$CO$_3$, between the substituted indole and the oxime of the ethyl-3-bromopyruvate ester (prepared in situ) to obtain an intermediate compound ethyl-3-(indole-3-yl)-2-hydroxylaminopropionate. From this intermediate are easily obtained both corresponding substituted tryptophan (by reduction with TiCl$_3$) and the derivative of indolepyruvic acid, by means of the hydrolytic hydrogenization with sodium hypophosphite, in the presence of Raney-Nickel catalysts in a buffered environment.

EXAMPLE 6

Synthesis of 3-indolepyruvic acid

By means of the second method of synthesis, it has also been possible to perfect a new and advantageous method for the synthesis of 3-indolepyruvic acid without substitutions, through the condensation reaction of the unsubstituted indole and ethyl-3-bromopyruvate ester oxime prepared in situ, and thus the hydrolytic hydrogenization of the intermediate compound with sodium hypophosphite in the presence of Raney-Nickel in a buffered environment.

The preparation is described herebelow.

840 mg of ethyl-3-bromopyruvate ester oxime were mixed with 940 mg of indole and 680 mg of anhydrous Na$_2$CO$_3$ in absolute dichloromethane. The oxime was prepared quantitatively according to the method of Ottenherjm, Tetrahedron Letters 5143, 1978. The mixture was then stirred at room temperature for approximately 12 hours. After having removed the solvent at reduced pressure, the residue was taken up with ethyl acetate and the whole was washed with water. Drying was performed on anhydrous magnesium sulphate, After having eliminated the drying means, concentration was carried out at low pressure and filtering was performed through silica with a mixture of petroleum ether (30/50)/ethyl acetate (1:1). After having eliminated by crystalization the indole, chromatography was performed on silica, recovering 869 mg of the oxyliminic derivative of ethyl-3-(indole-3-yl)-2-hydroxylimino propionate, with a yield of 80%. 490 mg of this compound were dissolved in 20 ml of ethanol/acetate buffer pH 5,0 (2:1). Under stirring was added an aqueous suspension of sodium hypophosphite (880 mg) containing Raney-Nichel (10 mg). This was brought under stirring to the temperature of approximately 50° C. for 3 hours. The reaction mixture was then filtered on celite and the solution was rapidly added dropwise and under energetic stirring to a large excess of HCl 1N, preheated to 55° C. (100 ml). After approximately 5 minutes from addition, a considerable precipitation of a canary-yellow colour was seen, which increased with time. Heating was continued for a further 15 minutes and the whole was then allowed to return to room temperature. After 3 hours the precipitate was filtered and then washed with acidic water. After drying 330 mg of 3-indolepyruvic acid were recovered, with a yield of 80%.

Pharmacological Tests

Several of the compounds according to the invention have undergone pharmacological tests to evidence their biological characteristics.

Given their similarity to indolepyruvic acid, these compounds have been compared to the latter in two experiments, which tend to verify the activities as radical scavengers and antagonists to excitatory amino acids.

For the first experiment was chosen the test on formation of malonodialdehyde (MDA). Briefly, the capacity was tested of the above compounds to antagonize the formation of free radicals from biological membrane undergoing oxidative stress.

For the second experiment, on the contrary, the capacity of the compounds to antagonize the convulsions and death induced by NMDA (N-methyl-D-aspartic acid), an excitatory amino acid, was evaluated.

In the following table the results obtained are shown.

| COMPOUND | MDA FORMATION IC50 | CONVULSIONS from MDA IC50 | DEATH from MDA IC50 |
|---|---|---|---|
| IPA | 1 × 10$^{-5}$ M | 200 mg/Kg ip | 50 mg/Kg ip |
| 4-Cl-IPA | 1 × 10$^{-3}$ M | 1000 mg/Kg ip | 200 mg/Kg ip |
| 5-Cl-IPA | 5 × 10$^{-4}$ M | 600 mg/Kg ip | 200 mg/Kg ip |
| 6-Cl-IPA | 1 × 10$^{-4}$ M | 20 mg/Kg ip | 10 mg/Kg ip |
| 7-Cl-IPA | 4 × 10$^{-4}$ M | 1000 mg/Kg ip | 200 mg/Kg ip |
| 6-OH-IPA | 5 × 10$^{-4}$ M | 800 mg/Kg ip | 200 mg/Kg ip |
| 6-Me-IPA | 6 × 10$^{-5}$ M | 200 mg/Kg ip | 100 mg/Kg ip |
| 6-Br-IPA | 5 × 10$^{-5}$ M | 100 mg/Kg ip | 20 mg/Kg ip |
| 6-OMe-IPA | 1 × 10$^{-4}$ M | 200 mg/Kg ip | 100 mg/Kg ip |
| 6-Cl-TRP | 1 × 10$^{-3}$ M | 1000 mg/Kg ip | 200 mg/Kg ip |

IPA = 3-indolepyruvic acid; TRP = Tryptophan; IC50 = dose of compound necessary to reduce by 50% the harmful effect to be added to the in vitro tests or to be administered to mice.

In these pharmacological tests, in vitro and in vivo, the compounds synthesized have shown themselves to possess characteristics for their development as inhibitors of the damage caused by free radicals and by excitatory amino acids.

It is equally evident that simple salts and esters of the above mentioned compounds have a similar behaviour.

The compounds can be pharmacologically employed in situations such as epilepsy, cerebral ischemia, ictus, Alzheimer's disease, cerebral deficiency of kynurenic acid.

The administration can be made by means of pharmacological compounds containing the active substance in a dose from 2 to 20 mg/Kg body weight in a "per os" or rectal administration, and in a dose from 1 to 10 mg/Kg body weight in a parenteral administration.

For oral, parenteral or rectal administration, the usual pharmaceutical forms can be used, such as pills, capsules, solutions, suspensions, injections, suppositories, in association with pharmaceutically acceptable vehicles or diluents and excipients.

We claim:

1. A process for the production of 3-indolepyruvic acid derivatives substituted on the benzene moiety, represented by formula I

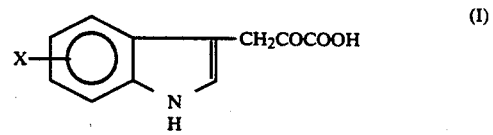

in which X is selected from the group consisting of hydrogen, halogen, methyl, methoxy and hydroxyl, comprising steps of:

transforming a substituted indole of the formula

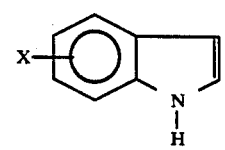

in which X is selected from the group consisting of hydrogen, halogen, methyl, methoxy and hydroxyl, into the corresponding substituted tryptophan by reacting the substituted indole with methylamine and formaldehyde in an aqueous solution, at a temperature not greater than about 5° C. to obtain the corresponding substituted gramine, then condensing said substituted gramine in a catalytic alkaline environment, in a per se known manner, with a derivative of malonic structure to obtain the corresponding substituted tryptophan, and transforming said substituted tryptophan into the corresponding substituted 3-indolepyruvic acid.

2. A process for the production of 3-indolepyruvic acid derivatives, substituted on the benzene moiety, represented by formula I

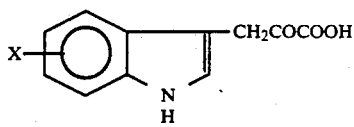
(I)

in which X is a substituent chosen from the group consisting of hydrogen, halogen, methyl, methoxy and hydroxyl, comprising the steps of:

(a) reacting in a condensation reaction a substituted indole of the formula

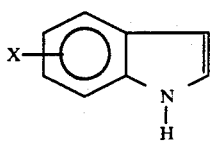

in which X is a substituent as defined for formula I, with a lower alkyl ester oxime of 3-bromo-pyruvic acid, having the structural formula

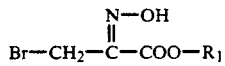

wherein R1 is a lower alkyl substituent, in a basic environment to obtain a lower alkyl-3-(substituted indole-3-yl)-2 hydroxylimine propionate as an intermediate compound having the structural formula

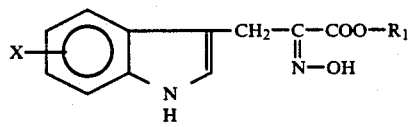

(b) reacting said intermediate compound in an aqueous solution containing TiCl$_3$ as a reducing agent to obtain a substituted tryptophan having the structural formula

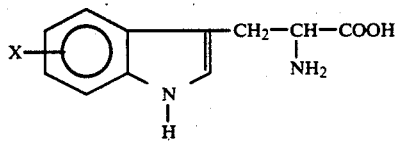

and (c) transforming said substituted tryptophan into the 3-indole pyruvic acid of formula I by reaction with an aromatic aldehyde in the presence of a basic, dehydrating proton acceptor agent in a solvent.

3. The process as recited in claim 2, wherein said basic, dehydrating proton acceptor agent is a tertiary amine base.

4. The process as recited in claim 2, wherein in step (c) said aromatic aldehyde is pyridine-carboxyaldehyde and said basic, proton acceptor agent is a mixture of 1,8 diazabicyclo-(5,4,0)-undec-7-ene and triethylamine and said solvent is methanol.

5. The process of claim 2, wherein said aromatic aldehyde is isonicotinaldehyde and said basic, proton acceptor agent is a mixture of 1,8 diazabicyclo-(5,4,0)-undec-7-ene and triethylamine and said solvent is methanol.

6. The process of claim 4, which further comprises recovering the indole-3-pyruvic acid by acidifying the reaction solution and collecting the resulting precipitate.

7. A process for the production of 3-indolepyruvic acid derivatives substituted on the benzene moiety, represented by formula I

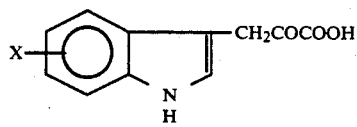
I in which X is a substituent chosen from the group consisting of hydrogen, halogen, methyl, methoxy and hydroxyl, comprising the steps of:

(a) reacting in a condensation reaction a substituted indole of the formula

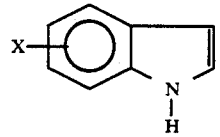

in which X is a substituent as defined for formula I, with a lower alkyl ester oxime of 3-bromo-pyruvic acid, having the structural formula

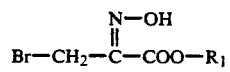

wherein R1 is a lower alkyl substituent, in a basic environment to obtain a lower alkyl-3-(substituted indole-3-yl)-2 hydroxylimine propionate as an intermediate compound having the structural formula

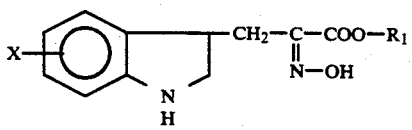

(b) reacting said intermediate compound in a buffered aqueous solution containing sodium hypophosphite as a hydrogenating agent, in the presence of a Raney-Nickel catalyst to obtain the substituted 3-indolepyruvic acid of formula I.

* * * * *